US010543370B2

(12) United States Patent
Doudna et al.

(10) Patent No.: US 10,543,370 B2
(45) Date of Patent: Jan. 28, 2020

(54) METHOD AND DEVICE TO MANAGE MODIFICATIONS OF PROTECTED REGISTERS IN AN IMPLANTABLE MEDICAL DEVICE

(71) Applicant: Pacesetter, Inc., Santa Clara, CA (US)

(72) Inventors: David Doudna, Sunnyvale, CA (US); Dean Andersen, San Jose, CA (US); Thomas Ng, Santa Clara, CA (US)

(73) Assignee: PACESETTER, INC., Sylmar, CA (US)

( * ) Notice: Subject to any disclaimer, the term of this patent is extended or adjusted under 35 U.S.C. 154(b) by 40 days.

(21) Appl. No.: 15/852,999

(22) Filed: Dec. 22, 2017

(65) Prior Publication Data
US 2019/0196734 A1    Jun. 27, 2019

(51) Int. Cl.
| | |
|---|---|
| *A61N 1/372* | (2006.01) |
| *G06F 3/06* | (2006.01) |
| *G06F 11/10* | (2006.01) |
| *A61N 1/368* | (2006.01) |
| *A61B 5/04* | (2006.01) |
| *A61N 1/37* | (2006.01) |

(52) U.S. Cl.
CPC ....... *A61N 1/37254* (2017.08); *G06F 3/0604* (2013.01); *G06F 3/0619* (2013.01); *G06F 3/0637* (2013.01); *G06F 3/0673* (2013.01); *G06F 11/1004* (2013.01); *A61B 5/04011* (2013.01); *A61N 1/3688* (2013.01); *A61N 1/3704* (2013.01); *A61N 1/37247* (2013.01)

(58) Field of Classification Search
CPC ........ A61N 1/25; A61N 1/08; A61N 1/37211; A61N 1/372; A61N 1/37; A61N 1/37254; A61N 1/3704; G06F 3/0619; G06F 3/0637
See application file for complete search history.

(56) References Cited

U.S. PATENT DOCUMENTS

| | | | | |
|---|---|---|---|---|
| 5,973,968 A | * | 10/1999 | Schu | .................. A61N 1/37211 365/195 |
| 6,128,528 A | * | 10/2000 | Ericksen | .................. A61N 1/37 607/2 |
| 6,141,774 A | | 10/2000 | Mattheis | |
| 7,013,178 B2 | * | 3/2006 | Reinke | .................... A61N 1/025 600/508 |
| 8,391,980 B2 | | 3/2013 | Bornzin et al. | |
| 8,473,069 B2 | * | 6/2013 | Bi | .......................... A61N 1/025 607/63 |
| 8,544,106 B2 | | 9/2013 | Haider et al. | |
| 8,831,747 B1 | | 9/2014 | Min et al. | |

(Continued)

*Primary Examiner* — Shelly A Chase
(74) *Attorney, Agent, or Firm* — Theresa A. Raymer

(57) ABSTRACT

Circuits, devices and methods are provided to manage modifications to protected registers within an implantable medical device (IMD). The circuit comprises a bus controller that includes an address register, an unlock register and a protected register (PR) enable unit. The PR enable unit sets a protect enable signal to an access state based on content loaded into the unlock register. A peripheral block includes a protected register that retains content for operating the IMD. The peripheral block includes a register access input to receive the protected enable signal. A PR write control unit is provided to enable an attempted write of the content from a data interface to the protected register when the protected enable signal has an access state.

22 Claims, 5 Drawing Sheets

(56) References Cited

U.S. PATENT DOCUMENTS

| | | |
|---|---|---|
| 9,044,610 B2 | 6/2015 | Rosenberg et al. |
| 9,216,285 B1 | 12/2015 | Boling et al. |
| 9,232,485 B2 | 1/2016 | Wu et al. |
| 9,333,351 B2 | 5/2016 | Arnold et al. |

* cited by examiner

METHOD AND DEVICE TO MANAGE MODIFICATIONS OF PROTECTED REGISTERS IN AN IMPLANTABLE MEDICAL DEVICE

BACKGROUND

Embodiments of the present disclosure generally relate to methods and devices to manage modifications of protected registers in implantable medical devices.

Implantable medical devices (IMDs) are configured to treat and/or monitor a variety of physiologic conditions. Non-limiting examples of IMDs include pacemakers, cardioverter defibrillators, cardiac rhythm therapy devices, neurostimulator devices, as well as various other implantable lead-based or leadless monitoring and/or therapy devices. An IMD operates based on various configuration settings that can programmed or otherwise set at the time of manufacture, at the time of implant and/or thereafter.

When designing an IMD, one goal is to build in safeguards against un-intended modifications to operation of the IMD, including the settings in certain registers, such as configuration registers. Configuration and other low-level settings are generally stored in memory elements referred to as registers. Changes in the settings in certain registers can substantially change an operation or state of the IMD. When the low-level registers are re-programmed in an unintended manner, the IMD may not perform the intended function or may perform an un-intended function.

Un-intentional modifications to a configuration register may be caused by various different sources. For example, a modification may be caused by a "soft error" or a 'hard fault". A hard fault corresponds to a physical change in the structure of the electronics, such as a broken wire. A soft error may cause one or more bits in a configuration register to change state. In general, an IMD may recover from a soft error if the error condition is detected. Soft errors may be triggered by normal ambient radiation which directly causes a state change (or "bit flip") in a latch, flip-flop, or memory cell. Optionally, the ambient radiation may not directly impinge upon the register, but instead may impact a component upstream of the register which in turn causes a downstream effect in which the register changes a state of one or more bits. Soft errors, while rare, do occur and can impact a system. Another source of un-intended modifications can be a software bug introduced either by accident or by malicious means in which an inadvertent write to a register or memory location can cause an undesired system impact.

It has been proposed to utilize a "redundant register" utility for certain registers that are expected to reliably hold a value for extended periods of time. The redundant register utility guards against both errant write operations and direct effects of radiation-induced single event upsets. However, the redundant register utility it is a costly resource solution as multiple addition logic components (e.g., flip-flops) are required to perform the check redundant operation.

In addition, it has been proposed to rely upon a simple parity check, whereby a single extra storage bit is added in connection with each register to be monitored. A state of the parity bit is managed to maintain a value that indicates whether a content of the registers is has a total number of odd or even "1"s (or "0" s). The use of a parity register provides some benefits. However, in many applications, a single parity bit is insufficient due to a vulnerability that a pair or an even number of bits in the register may change to incorrect states.

SUMMARY

In accordance with embodiments herein, a circuit is provided to manage modifications to protected registers within an implantable medical device (IMD). The circuit comprises a bus controller that includes an address register, an unlock register and a protected register (PR) enable unit. The PR enable unit sets a protect enable signal to an access state based on content loaded into the unlock register. A peripheral block includes a protected register that retains content for operating the IMD. The peripheral block includes a register access input to receive the protected enable signal. A PR write control unit is provided to enable an attempted write of the content from a data interface to the protected register when the protected enable signal has an access state.

Optionally, the unlock register may be configured to receive a code authorizing a modification to a protected register having an address stored in the address register. The bus controller may direct content conveyed over the data interface to one or more registers designated by the address register. The one or more registers may include the protected register. The PR enable unit may include a comparator to compare the content loaded into the unlock register with content loaded in the address register. The PR enable unit may set the protect enable signal to the access state when the content of unlock and address registers match. The PR enable unit may set the protect enable signal to a deny state when the content of the unlock and address registers differ.

Optionally, the bus controller may automatically clear the unlock register, once the unlock register content is analyzed, to avoid analyzing the content of the unlock register associated with a first PR write request during a later second PR write request. The peripheral block may comprise a parity register that may be configured to be set to a coherent value based on content of the protected register. A comparator may compare content of the parity register and the protected register in connection with validating the content of the protected register. The peripheral block may comprise a parity register control unit that may set a content of the parity register to an incoherent value when the protected register is reset to a default content. The incoherent value may represent an opposite of a coherent value corresponding to the default content.

In accordance with embodiments herein, an implantable medical device is provided. The device comprises a housing enclosing memory, a processor and a protection circuit. An electrode combination is configured to sense physiologic signals or deliver a therapy. Memory within the housing stores program instructions in connection with at least one of monitoring physiologic signals or delivering therapy. A processor is configured to execute the program instructions in connection with detecting physiologic signals along one or more sensing vectors defined by the electrode combination. The protection circuit comprises a bus controller including an address register, an unlock register and a protected register (PR) enable unit. The PR enable unit sets a protect enable signal to an access state based on content loaded into the unlock register. A peripheral block includes a protected register to retain content for operating the IMD. The peripheral block includes a register access input to receive the protected enable signal. A PR write control unit enables an attempted write of the content from a data interface to the protected register when the protected enable signal has an access state.

Optionally, the bus controller may direct content conveyed over the data interface to one or more registers designated by the address register. The one or more registers may include the protected register. The PR enable unit may include a comparator to compare the content loaded into the unlock register with content loaded in the address register. The PR enable unit may set the protect enable signal to the access state when the content of unlock and address registers match. The PR enable unit may set the protect enable signal to a deny state when the content of the unlock and address registers differ. The peripheral block and bus controller may be formed on a common integrated circuit.

Optionally, the bus controller may automatically clear the unlock register, once the unlock register content is analyzed, to avoid analyzing the content of the unlock register associated with a first PR write request during a later second PR write request. The peripheral block may further comprise a parity register that may be configured to be set to a coherent value based on content of the protected register. A comparator may compare content of the parity register and the protected register in connection with validating the content of the protected register. The peripheral block may further comprise a parity register control unit that sets a content of the parity register to an incoherent value when the protected register is reset to a default content. The incoherent value may represent an opposite of a coherent value corresponding to the default content.

In accordance with embodiments herein, a method is provided to manage modifications to protected registers within an implantable medical device (IMD). The method retains first content in a protected register (PR) for operating the IMD, receives a PR write request representing an attempted write of second content to the protected register, analyzes content of an unlock register associated with the protected register, sets a protect enable signal to an access state or a deny state based on the content loaded into the unlock register and enables the attempted write of the second content to the protected register when the protected enable signal has the access state.

Optionally, the analyzing may comprise comparing the content of the unlock register to an address in an address register. The address designates the protected register. Optionally, before the analyzing operation, the method may further comprise i) saving an initial content of the unlock register on an interrupt stack, the initial content independent of the PR write request; and ii) writing unlock content to the unlock register over the initial content. Next, after enabling the attempted write of the second content, the method may pop the initial content from the interrupt stack and reload the initial content to the unlock register. The method may automatically clear the unlock register to avoid analyzing the content of the unlock register associated with a first PR write request during a later second PR write request.

DETAILED DESCRIPTION

Figure 1:
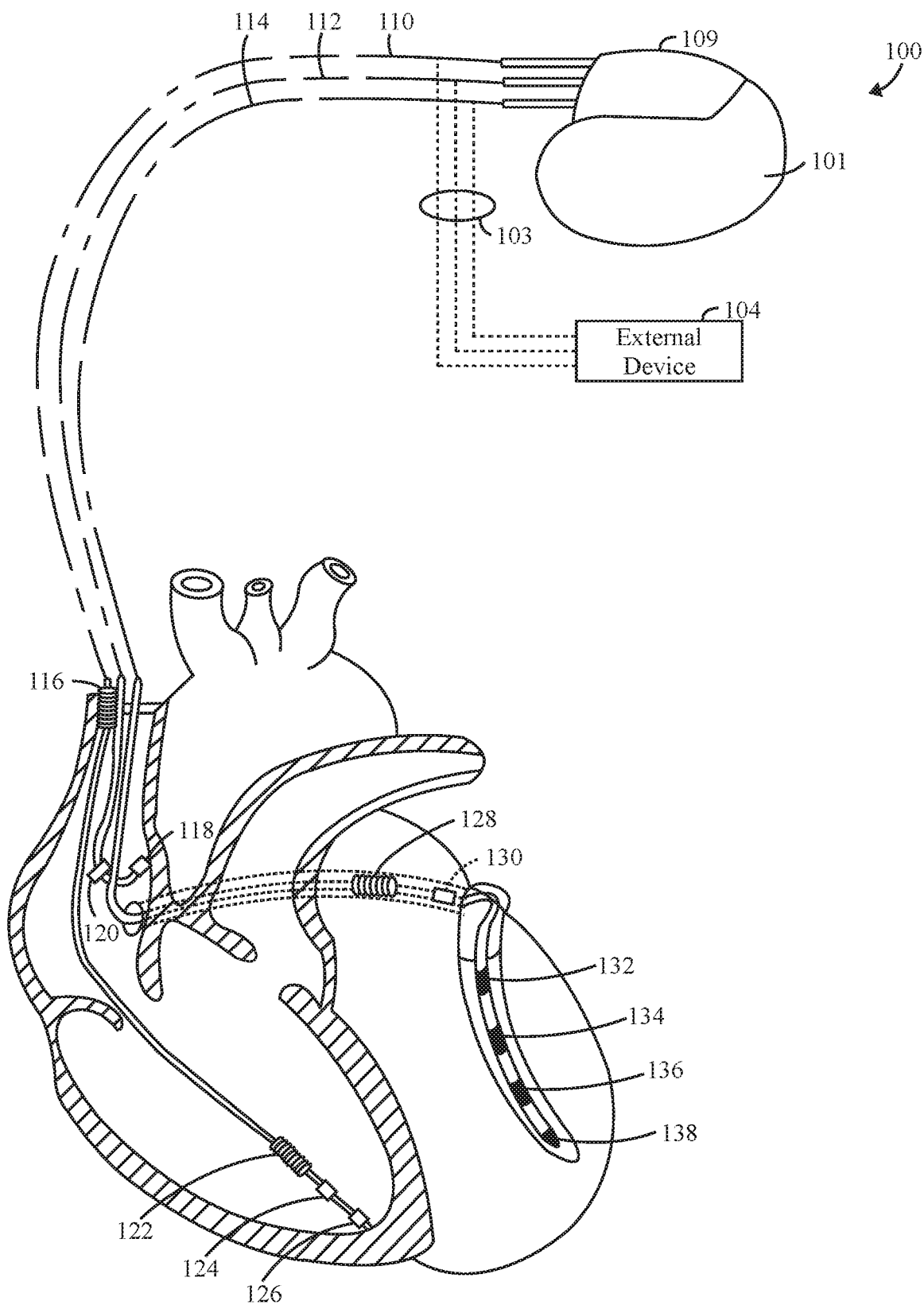
FIG. 1 illustrates an IMD and external device coupled to a heart in a patient and implemented in accordance with one embodiment.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMB may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the 1 MB may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Embodiments herein provide methods and devices to protect against errant write operations. A protection circuit is provided that requires an unlock code to be loaded to a separate, specific location prior to writing new data to a register of interest (e.g., a configuration register). If the unlock code is correct, a protection circuit allows the write to the register. If the unlock code is incorrect, the protection circuit denies the write to the register. Optionally, the protection circuit may manage unlock codes such that a particular unlock code is only maintained valid for one write operation or a limited number of write operations. Thereafter, the same or a new unlock code would need to be loaded before performing further write operations to the same or another register of interest. For example, the protection circuit provides a two-step process to be followed before allowing data to be written to configuration registers. The protection circuit provides a new protection implementation that is robust, while avoiding a need for additional firmware to enforce register write protection (e.g., with specific assembly instructions or making the write sequence immune to interrupts by placing it in a critical section). Optionally if the unlock code is incorrect, the details of the attempted unlock may be stored in memory as a diagnostic record. The details may include the value of the data attempting the unlock transaction, the address of the attempted configuration register and the time of the attempted unlock. Further escalation of the attempted unlock may result in a reset of the program code or entire system.

Optionally, the protection circuit may utilize parity bit protection in addition to the two-part unlock process. For example, parity bit protection may be applied to separate registers. As one non-limiting example a register may have up to 32 bits. The parity is checked periodically (usually several times a second) to ensure none of the bits in the register have changed state since the last check. By way of example, the latches/flip-flops of an individual configuration register may be located at physically separate (non-adjacent) locations. By physically scattered the latches/flip-flops, along with a parity check, embodiments herein provide added protection against single event upsets.

Terms

The term "register" is used to refer to memory elements that are utilized during operation of an IMD to define basic IMD behavior. A non-limiting example of a register may be an array of flip-flops, latches or memory cells that are set to predetermined states corresponding to particular settings, such as a configuration setting. Non-limiting examples of registers include configuration registers to set a trim value for clock frequency, a reference power supply voltage, a therapy, a safety-mode therapy, wireless telemetry communications, and the like.

The terms "coherent" and "incoherent" are used in connection with describing parity. A system may be designated to have even parity of "1" bits, or odd parity of "1" bits. When using even parity, the content of a register is "coherent" when the content of the register has an even number of "1" bits. When the content of a register does not match the parity of the system, the content of the register is considered incoherent. For example, when using even parity of "1" bits, the content of a register is "incoherent" when the content of the register has an odd number of "1" bits.

FIG. 1 illustrates an IMD 100 and external device 104 coupled to a heart in a patient and implemented in accordance with one embodiment. The external device 104 may be a programmer, an external defibrillator, a workstation, a portable computer, a personal digital assistant, a cell phone, a bedside monitor and the like. The IMD may represent a cardiac monitoring device, pacemaker, cardioverter, cardiac rhythm management device, defibrillator, neurostimulator, leadless monitoring device, leadless pacemaker and the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and then transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
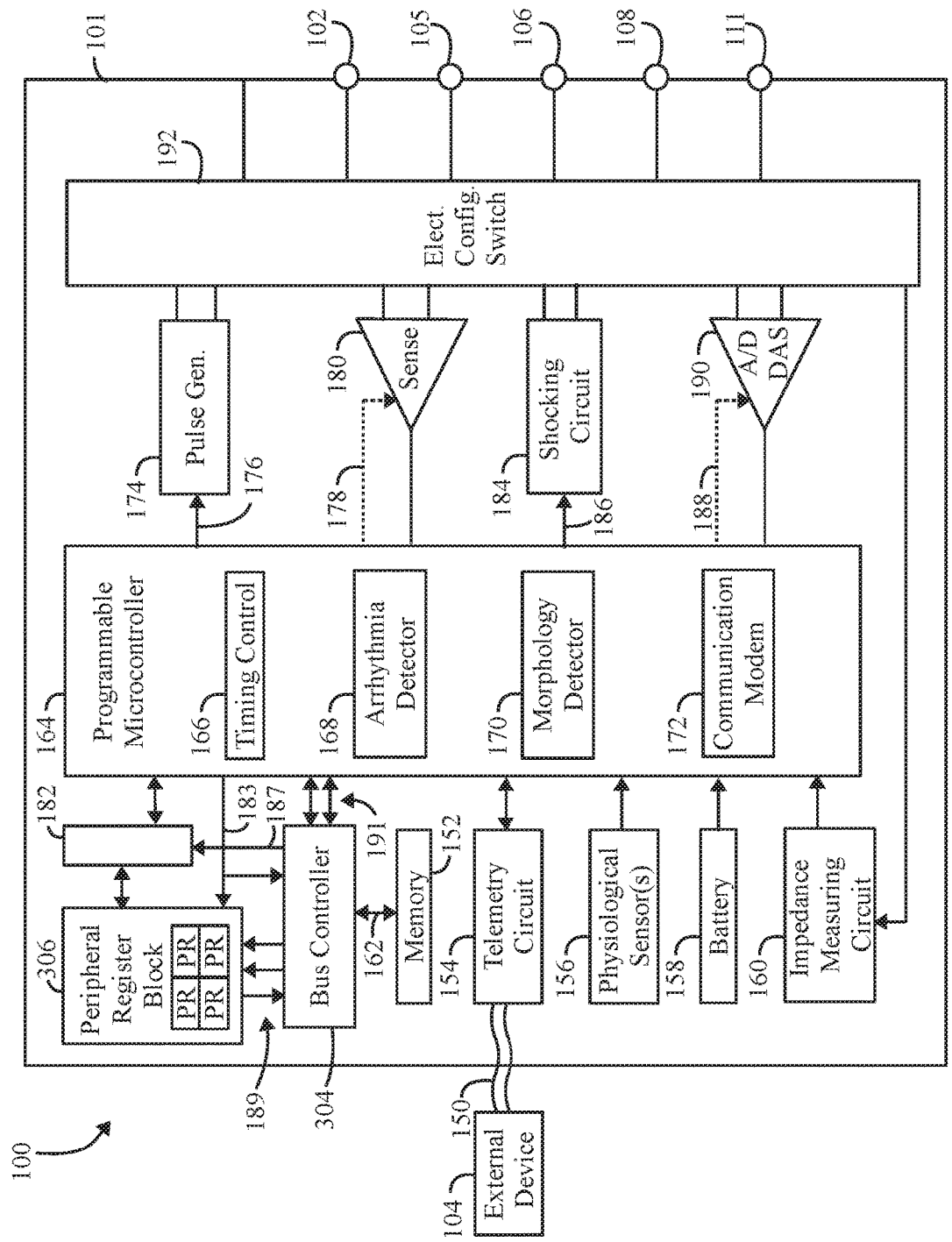
FIG. 2 illustrates a block diagram of the IMD in accordance with embodiments herein.

FIG. 2 illustrates a block diagram of the IMD 100 of FIG. 1. The IMD 100 has a housing 101 to hold the electronic/computing components. The housing 101 (which is often referred to as the "can", "case", "encasing", or "case electrode") may be programmably selected to act as the return electrode for certain stimulus modes. Housing 101 further includes a connector (not shown) with a plurality of terminals 102, 105, 106, 108, and 111. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 111 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes a microprocessor (or equivalent control circuitry), RAM and/or ROM memory, logic and timing circuitry, state machine circuitry, and I/O circuitry.

IMD 100 further includes a first chamber pulse generator 174 that generates stimulation pulses for delivery by one or more electrodes coupled thereto. The pulse generator 174 may deliver pacing pulses and/or anti-tachy pacing therapy. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164.

The IMD 100 is further equipped with a communication modem (modulator/demodulator) 172 to enable wireless communication with other devices, implanted devices and/or external devices. The communication modem 172 may be implemented in hardware as part of the microcontroller 164, or as software/firmware instructions programmed into and executed by the microcontroller 164. Alternatively, the modem 172 may reside separately from the microcontroller as a standalone component.

The IMD 100 includes sensing circuitry 180 selectively coupled to one or more electrodes that perform sensing operations, through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

The IMD 100 further includes an analog-to-digital (A/D) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The IMD 100 can further include one or more physiologic sensors 156. Such sensors are commonly referred to as "rate-responsive" sensors because they are typically used to adjust pacing stimulation rates according to the exercise state of the patient. The microcontroller 164 responds by adjusting the various pacing parameters (such as rate, AV Delay, V-V Delay, etc.) at which the atrial and ventricular pacing pulses are administered. While shown as being included within the unit 100, the physiologic sensor(s) 156 may be external to the unit 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the unit 100 employs lithium/silver vanadium oxide batteries.

Optionally, the IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used. Optionally, the microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 111 to 40 joules), as controlled by the microcontroller 164.

Microcontroller 164 is illustrated to include timing control circuitry 166 to control the timing of the stimulation pulses (e.g., pacing rate, atrio-ventricular (AV) delay, atrial interconduction (A-A) delay, or ventricular interconduction (V-V) delay, etc.). The timing control circuitry 166 may also be used for the timing of refractory periods, blanking intervals, noise detection windows, evoked response windows, alert intervals, marker channel timing, and so on. Microcontroller 164 also has an arrhythmia detector 168 for detecting arrhythmia conditions and a morphology detector 170 to review and analyze one or more features of the morphology of cardiac signals. Although not shown, the microcontroller 164 may further include other dedicated circuitry and/or firmware/software components that assist in monitoring various conditions of the patient's heart and managing pacing therapies.

A bus controller 304 is coupled to a memory 152 by a suitable data/address bus 162. The bus controller 304 generally decodes the address from the microcontroller 162 and determines the location whether the location is in memory 152, on a peripheral circuit or elsewhere. The memory 152 stores, among other things, one or more interrupt stacks that save the content of registers during interrupt operations. For example, when a register write request has initiated but is then interrupted, the interrupt stack will store the content of one or more registers utilized during the write request. Once the interrupt operation is over and the write request is re-instated, the register content "popped" off the stack and reloaded into the corresponding registers. The programmable operating parameters used by the microcontroller 164 are stored in memory 152 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy. The operating parameters of the IMD 100 may be non-invasively programmed into the memory 152 through a telemetry circuit 154 in telemetric communication via communication link 150 with the external device 104. The telemetry circuit 154 allows intracardiac electrograms and status information relating to the operation of the IMD 100 (as contained in the microcontroller 164 or memory 152) to be sent to the external device 104 through the established communication link 150.

The microcontroller 164 is coupled to a peripheral block 306 (also referred to as a peripheral register block or PRB) through one or more buses 182 and one or more control lines 183. Access to the bus 182 is managed by a bus controller (BC) 304 over a bus control line 187. The bus controller 304 communicates with the peripheral block 306 over PRB control lines 189. Non-limiting examples of PRB control lines 189 include a data interface, a protect enable signal, a protect parity inhibit signal and a slave error signal (as described below). The microcontroller 164 communicates with the bus controller 304 over BC control lines 191 (e.g., an IC test enable signal). The peripheral block 306 includes one or more protected registers (PR) that store data utilized during basic operations of the IMD 100 such as to define configuration settings for the IMD 100. As explained hereafter, the peripheral block 306 and bus controller 304 cooperate to implement a protection circuit to manage modifications to one or more of the protected registers on the PRB. The microcontroller 164, peripheral block 306 and bus controller 304 may be formed on a common integrated circuit, such as in a system on a chip (SOC) integrated circuit.

Register Protection Circuit

Figure 3:
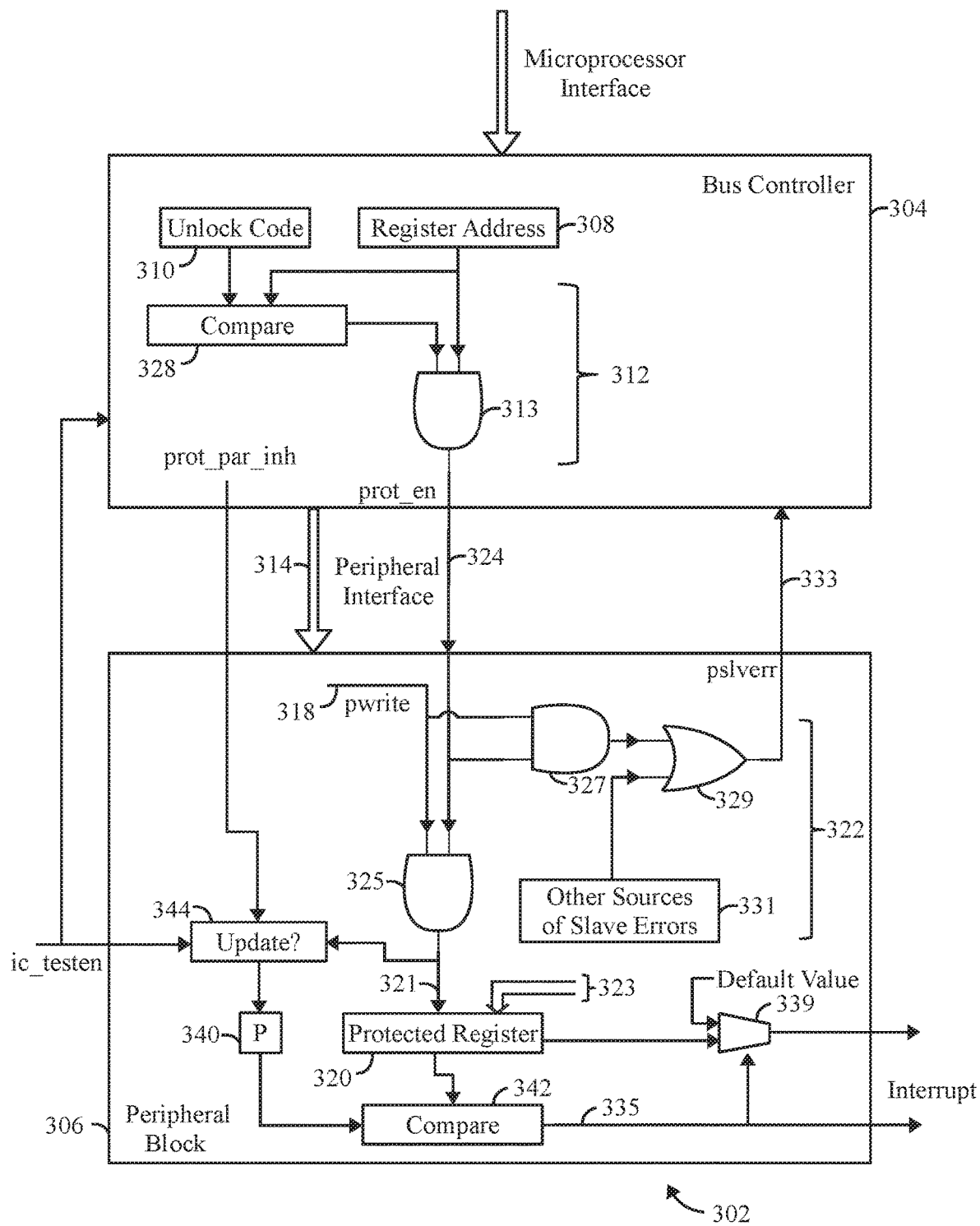
FIG. 3 illustrates a block diagram of a protection circuit formed in accordance with an embodiment herein.

FIG. 3 illustrates a block diagram of a protection circuit 302 formed in accordance with an embodiment herein. The protection circuit 302 is configured to manage modifications to one or more configuration registers within the IMD. The protection circuit 302 includes all or aspects of the bus controller 304 and peripheral block 306. The bus controller 304 includes an address register 308, an unlock register 310 and a protected register (PR) enable unit 312. The unlock register 310 is configured to receive unlock validation data. For example, the unlock validation data may be an address that is common to an address stored in the address register. The bus controller 304 analyzes the unlock validation data to determine whether a protected register should be "unlocked" and enabled to receive new data (e.g., to be written to). In connection with an unlocking operation, the PR enable unit 312 sets a protect enable signal 324 to an access state based on content loaded into the unlock register.

The bus controller 304 directs content conveyed over a data interface 314 to one or more registers (including a protected register 320) designated by the address register 308. For example, the data interface 314 may correspond to the data path through the bus 182 (FIG. 2) between the microcontroller 164 and the PRB 306. The PR enable unit 312 includes a comparator 328 and an AND gate 313. The comparator 328 is configured to compare the content loaded into the unlock register 310 with content loaded in the address register 308. The AND gate 313 receive as inputs, an output from the address register 308 and an output from the comparator 328. When both inputs of the AND gate 313 are high, the AND gate 313 sets an output to a high state. Accordingly, the PR enable unit 312 sets the protect enable signal 324 to the access state when the content of the unlock register 310 and address register 308 correspond to one another (e.g., match). The PR enable unit 312 sets the protect enable signal 324 to a deny state when the content of unlock and address registers 310, 308 do not correspond (e.g., differ from one another).

The peripheral block 306 includes the data interface 314 that is configured to receive certain types of data such as configuration data. The peripheral block 306 also includes the protected register 320 that is configured to retain certain data such as configuration data for operating the IMD. The peripheral block 306 also includes a register access input that is configured to receive the protected enable signal 324. A PR write control unit 322 is configured to enable an attempted write from the data interface 314 to write configuration data to the protected register 320 when the protected enable signal 324 is set to the access state. In addition, the PR write control unit 322 is configured to deny/block an attempted write from the data interface 314 to the protected register 320 when the protected enable signal 324 is set to the deny state.

By way of example, the PR write control unit 322 includes an AND gate 325 that receives as inputs a write (PWRITE) signal 318 and the protect enable signal 324 (PROT_EN). The write signal 318 may be provided by the microcontroller 164, while the protect enable signal 324 is delivered through a register access input. When both inputs to the AND gate 325 are high, the AND gate 325 outputs a high signal that is passed as an access control input 321 of the protected register 320 and to the parity control unit 344. The access control input 321 locks and unlocks write operations to the protected register. Once the protected register 320 is unlocked, new content may be loaded over a data interface 323. The write signal and protect enable signal 324 are also delivered as inputs to an AND gate 327 with one input inverted. An output of the AND gate 327 is provided as an input to an OR gate 329. The OR gate 329 also receives, as an input, a signal from other sources of slave errors 331. The AND gate 327 is configured to identify when a PWRITE request is present that lacks an asserted protect enable PROT_EN. When the write signal 318 and protect enable signal 324 have opposite values, the NOR gate 327 outputs a high signal. When either or both inputs of the OR gate 329 have high values, the OR gate 329 outputs a high signal which represents a slave error signal 333.

Additionally or alternatively, the peripheral block 306 may further comprise a parity register 340 that is configured to be set to a coherent value based on content of the protected register 320. A comparator 342 is configured to compare content of the parity register 340 and the protected register 320 in connection with validating the content of the protected register 320. The peripheral block 306 may further comprise a parity control unit 344 that sets a content of the parity register 340 to an incoherent value when the protected register 320 is reset to a default value.

An expected parity, that is calculated from the data content of the protected register 320, is compared against the stored parity register (bit) 340 associated with the protected register 320. When a mismatch occurs, a configuration register fault interrupt event is generated at the comparator 342 as an interrupt signal 335 which is delivered from the peripheral block 306 to the microcontroller 164. Optionally, configuration register fault interrupt signal 335 may be masked upon a global master hardware reset.

Optionally, an instantiation option may be provided to permit selection of whether a corresponding protected register changes all or a portion of the content therein to a reset default value when the parity control unit 344 determines an incoherence in parity.

Optionally, the peripheral block 306 may include an optionally multiplexer 339 that receives, as inputs, a default value and the content of the protected register 320. The output of the comparator 342 is provided as a control signal to the multiplexer 339 to switch the multiplexer 339 between the default value and the content of the protected register 320.

Figure 4:
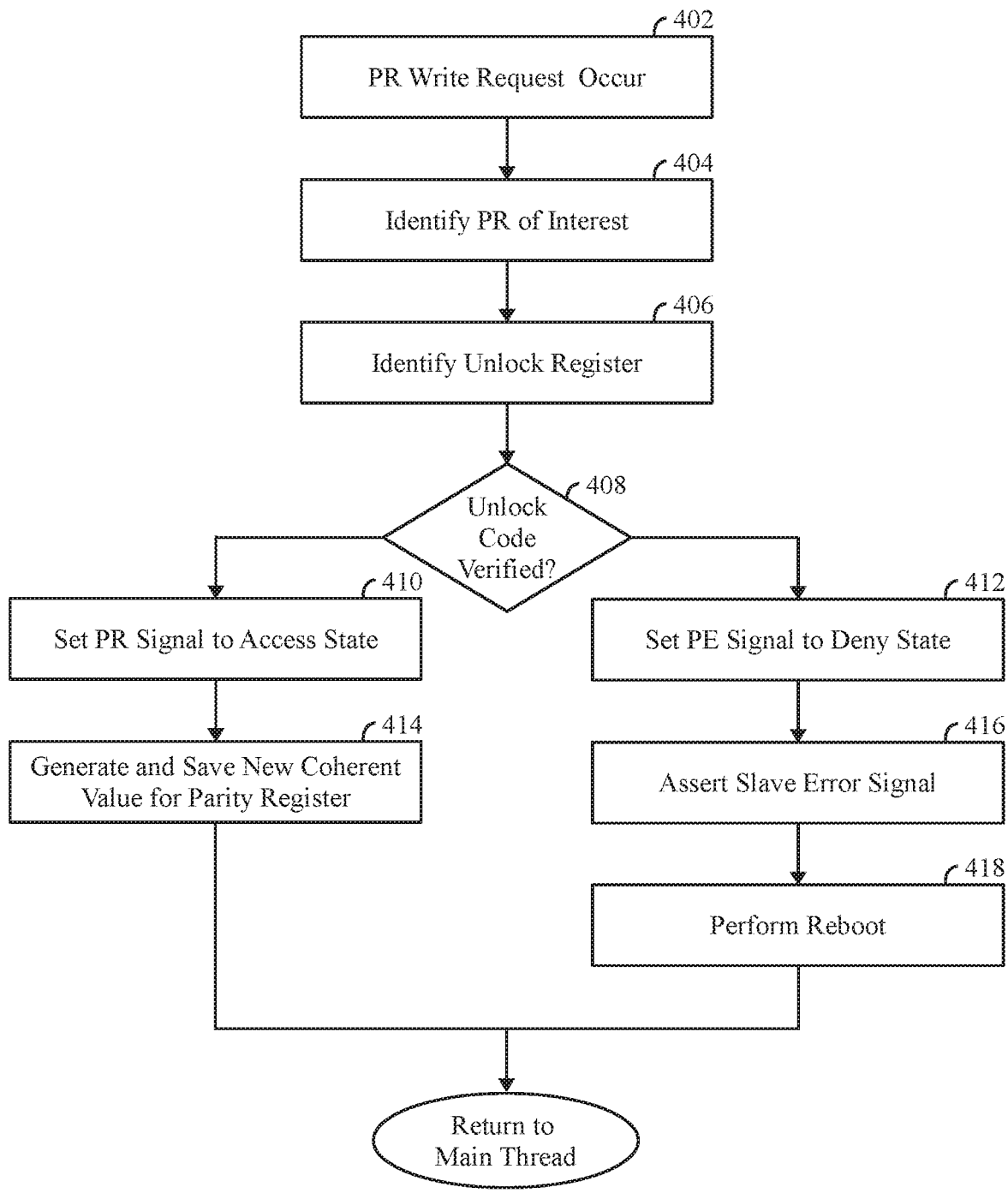
FIG. 4 illustrates a flow chart for implementing a register protection process in accordance with embodiments herein.

FIG. 4 illustrates a flow chart for implementing a register protection process in accordance with embodiments herein. The operations of FIG. 4 may be implemented by firmware as a background task thread. By implementing the operations as a background task thread, embodiments herein avoid disabling primary functionality of the IMD, such as monitoring physiologic behavior, delivering therapy and the like.

At 402, the process determines that a PR write request has occurred. For example, the microcontroller 164 may initiate a PR write request based on various criteria. Additionally or alternatively, the PR write request may result from a command or instruction received by the 1 MB from an external device (e.g., an external programmer, a home monitoring device, a patient/physician handheld electronic device, etc.). At 404, the process identifies the protected register of interest, to which the PR write request relates. For example, the PR write request may designate a unique address associated with the protected register of interest. Additionally or alternatively, the PR write request may indicate a nature or characteristic of the protected register and/or a nature or characteristic of the content to be written to the protected register. For example, the PR write request may include, or be preceded by, a code or bit that designates the nature/characteristic of the content (e.g., clock update, reference power source).

At 406, the process identifies one or more unlock registers associated with a protected register of interest. For example, a separate unlock register may be provided in connection with each protected register. Additionally or alternatively, an unlock register may be provided in connection with multiple protected registers. Additionally or alternatively, a subset of unlock registers may be provided in connection with a larger set of protected registers. In accordance with embodiments herein, the unlock register(s) may be located on the same board or component that is utilized to access a protected register, such as on a bus controller that includes one or more address registers (e.g., as shown in FIG. 3). Optionally, the unlock register(s) may be located on a same board or component as the related protected register, such as the peripheral block (e.g., as shown in FIG. 3). During a valid PR write request, an unlock code is written to the unlock register at 406. As explained hereafter, no content or content, other than an unlock code, may be written to the unlock register.

At 408, the process analyzes a content of the unlock register to verify whether the unlock register has been loaded with a valid unlock code. A valid unlock code may be loaded into the unlock register before, as part of, or after the PR write request occurs. The analysis at 408 may be performed by a comparator circuit on the bus controller. Additionally or alternatively, the comparator circuit may be physically located elsewhere in the 1 MB. Optionally, the analysis may be performed by other circuits in addition to, or instead of, a comparator circuit. For example, the analysis at 408 may be performed by the microcontroller 164, such as by reading the content of the unlock register and comparing the unlock register content to an unlock code. The unlock code may be defined in various manners. For example, the unlock code may be defined to correspond to the address of the protected register. Optionally, the unlock code may be defined to match a predefined security key that is only available to authorized personnel. Optionally, embodiments may utilize rolling codes that randomly change periodically.

A valid unlock code should be written to the unlock register before the process will enable a write operation to a protected register. In the example of FIG. 3, the unlock register 310 receives an unlock code, such as the address of the protected register 320. The address of the protected register 320 is also written to the protected address register (e.g., 308 in FIG. 3). The comparator circuit 328 compares the addresses in the unlock register 308 and the address register 310.

At 408, when a match exists, flow branches to 410 where a protect enable (PE) signal 324 is set to an access state. For example, when the comparator sets the PE signal to the access state (e.g., PROT_EN asserted/high), the PR write control unit 322 accepts a new value for the protected register. At 414, the parity control unit automatically generates and saves a new coherent value (e.g., bit) in the parity register 340.

At 408, when a match does not exist, flow branches to 412 where the protect enable signal 324 is set to a deny state (e.g., PROT_EN not asserted/low). When an attempt is made to write to a protected register without PROT_EN asserted, the PR write control unit 322 rejects the attempted write and preserves the existing value in the protected register 320. At 416, the process asserts a "Slave Error" signal (e.g., PSLVERR). Optionally, the slave error signal may be utilized by the bus controller 304 and/or passed to the microcontroller 164 to be utilized in various manners. For example, the slave error signal may be utilized to inform the microcontroller 164 that a PR write request was not performed. The slave error signal may be logged for future reference. Optionally, at 418, a reboot operation may be performed in response to assertion of the slave error signal. During a reboot operation in response to a slave error signal, the firmware reset handler interrogates both i) the address in the address register 308 associated with the rejected write and ii) the content in the unlock register 310. In the foregoing example, the unlock register 310 is reset by hardware during a reboot operation that is performed in response to a slave error signal. The content of the unlock register 310 may be reset during other reboot operations, such as in connection with a power-on reset. After the firmware reset handler (within the microcontroller 164) interrogates the unlock register 310, the reset handler resets the unlock register as part of the rebooting process. Optionally, the reboot operation may be omitted.

The operations at 402-418 represent one transaction or write request. Once the unlock register content is analyzed, the hardware automatically clears the unlock register. A PR write request may initiate the process of FIG. 4 without any unlock code or without a valid unlock content being written to the unlock register, although such as a PR write request would be invalid/improper. Accordingly, in accordance with some embodiments, the process clears the unlock register at 408 to avoid analyzing the content of the unlock register associated with a first PR write request to be considered again during a later second PR write request.

As noted above, the process of FIG. 4 may be interrupted at any point by a higher priority interrupt. When the higher priority interrupt ends, flow returns to FIG. 4.

Optionally, the process of FIG. 4 may also include a parallel unlock register management process for managing content of the unlock register. For example, before writing to a protected register, the process may first read an initial content of one or more unlock registers and save the content of the one or more unlock registers to an interrupt stack in memory. The initial content that is read from the unlock register is independent of, and separate and distinct from, a current PR write request. As one example, the initial content may simply represent a null value. The initial content is maintained on the interrupt stack for at least a portion of the duration of the PR write request as described herein. Once the initial content of the unlock register is saved or pushed to a corresponding stack, unlock code/content may be written to the unlock register over the initial content. During a valid PR write request, a valid unlock code would be written to the unlock register. As noted herein, the valid unlock code may take various forms, such as an address of a protected register, rolling codes or other types of codes to define a valid unlock code. After completing the PR write request to the protected register, the unlock register management process continues by "popping" the saved initial content from the stack and restoring the initial content to the unlock register.

The unlock register management process operates in parallel with or more generally "surrounds" the protected register writing process of FIG. 4. For example, the initial content of the unlock register may be pushed/saved to a stack before, during or after one or more of the operations at 402, 404 and 406. The initial content may then be popped from the stack and restored to the unlock register at any point in the process of FIG. 4 after the verification at 408.

The unlock register management process provides a rigorous protocol that facilitates compatibility of the process of FIG. 4 with multithreaded architectures that switch between execution threads through interrupts, while avoiding a need for firmware to enforce atomicity (e.g. with specific assembly instructions or making the write sequence immune to interrupts by placing it in a "critical section" with interrupts disabled).

Figure 5:
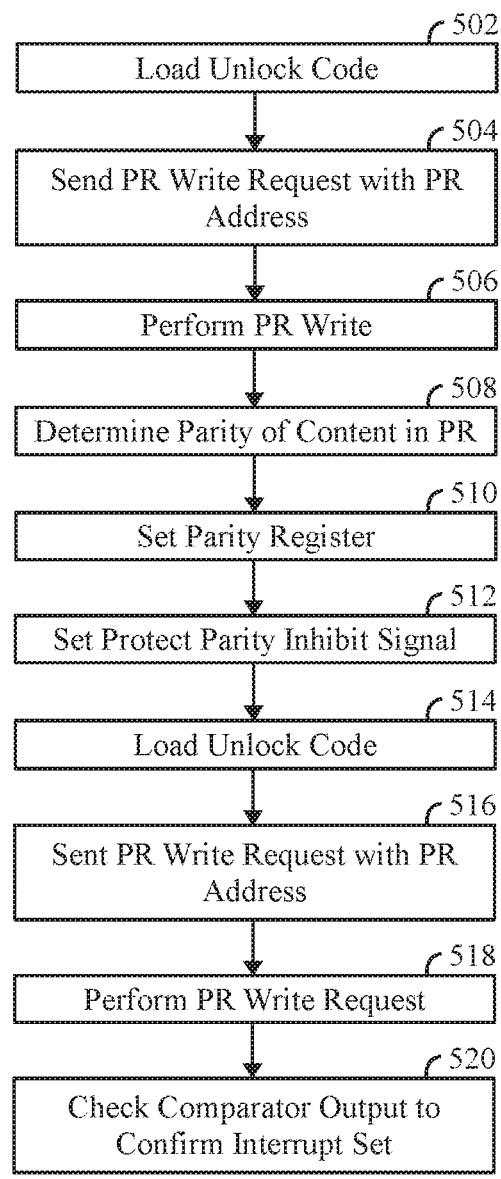
FIG. 5 illustrates a process for testing a parity maintenance circuit in accordance with embodiments herein.

FIG. 5 illustrates a process for testing a parity maintenance circuit in accordance with embodiments herein. The operations of FIG. 5 will be described in connection with the protection circuit of FIG. 3 by way of example only. It is understood that the parity testing process of FIG. 5 may be implemented in connection with protection circuits having alternative structures. By way of example, the parity testing may be performed under control of the microcontroller 164 (FIG. 3) which provides instructions to the parity control unit 344. At 502, the process loads an unlock code into the unlock register 310. At 504, the microcontroller 164 sends a PR request with an address for a protected register to be tested. The address of the protected register is loaded into the register address 308. At 506, the protection circuit 302 performs a valid PR write operation to the protected register 320, wherein the content written to the protected register 320 corresponds to a predetermined message having a known parity. For example, when parity is even, the content written to the protected register 320 may be predetermined to have even parity.

At 508, the parity control unit 344 determines the parity of the content loaded in the protected register. At 510, the PR control unit sets the parity register 340 based on the parity of the content determined at 508. For example, when the content in the protected register is determined at 508 to have even parity, the parity control unit 344 may set the parity register 340 to a high or "one" value. Alternatively, when the content in the protected register is determined to have odd parity, the parity control unit 344 sets the parity register 340 to a low or "zero" value.

At 512, the microcontroller sets a protect parity inhibit signal (PROT_PAR_INH) to disable the parity control unit 344, thereby preventing the parity control unit 344 from changing the parity register 340. At 514, the microcontroller 164 loads a new unlock code into the unlock register 310. At 516, the microcontroller 164 sends a new PR write request with the address of the same protected register as updated at 502-506. At 518, the protection circuit 302 performs the PR write request. The microcontroller 164 manages the content associated with the new PR write request at 516 to have an opposite parity as the content associated with the first write request at 504. For example, when the content associated with a first write request at 504 is even, the microcontroller 164 will define the content of the second PR write request at 516 to be odd.

At 520 the comparator 342 calculates the expected parity that should be associated with the content of the protected register as updated at 518. The comparator 342 compares the expected parity with the content of the parity register 340. Given that the protect parity inhibit signal was set at 512, following the write operation at 518, the parity control unit 344 does not change the content of the parity register 340. Accordingly, the parity register 340 is incorrect. When operating correctly, the comparator 342 should set an interrupt signal indicating that the parity register is incorrect.

In accordance with the operations of FIG. 5, a design-for-test feature may be provided through management of a global protect parity inhibit signal. The global PROT_PAR_INH signal is asserted during a valid protected register write. Consequently, the protection circuit accepts the new content into the protected register while retaining the existing value held in the parity register (e.g., bit). By way of example, the protect parity inhibit signal may be asserted during an IC test mode (e.g., at the time of manufacture, or during system updates).

Optionally, during a reset operation, the parity register may be set to a default value when the protected register is reset (e.g., by a global master hardware reset, the power-on reset or otherwise). For example, the default value may correspond to a default incoherent value wherein the parity bit has a value opposite to a parity bit associated with a coherent value. By setting the parity register to an incoherent value at the time of reset, embodiments herein force the firmware to make an explicit choice for all of the protected registers on the peripheral block before unmasking the respective incoherency interrupt.

Optionally, a protected register may be assigned default content that is coherent. For example, a new protected register may be assigned a coherent default value coherent when it needs to be ignorable, such as in an enhancement to an existing product where it is desirable to not impact the firmware.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A circuit to manage modifications to protected registers within an implantable medical device (IMD), comprising:
   a bus controller including an address register, and unlock register and a protected register (PR) enable unit, the PR enable unit to set a protect enable signal to an access state based on content loaded into the unlock register; and a peripheral block including a protected register to retain content for operating the IMD, the peripheral block including a register access input to receive the protected enable signal; and a PR write control unit to enable an attempted write of the content from a data interface to the protected register when the protected enable signal has an access state, wherein the peripheral block further comprises:

a parity register configured to be set to a coherent value based on content of the protected register; and a comparator to compare content of the parity register and the protected register in connection with validating the content of the protected register.

2. The circuit of claim 1, wherein the unlock register is configured to receive a code authorizing a modification to a protected register having an address stored in the address register.

3. The circuit of claim 1, wherein the bus controller directs content conveyed over the data interface to one or more registers designated by the address register, the one or more registers including the protected register.

4. The circuit of claim 1, wherein the PR enable unit includes a comparator to compare the content loaded into the unlock register with content loaded in the address register, the PR enable unit setting the protect enable signal to the access state when the content of unlock and address registers match.

5. The circuit of claim 4, wherein the PR enable unit sets the protect enable signal to a deny state when the content of the unlock and address registers differ.

6. The circuit of claim 1, wherein the bus controller to automatically clear the unlock register, once the unlock register content is analyzed, to avoid analyzing the content of the unlock register associated with a first PR write request during a later second PR write request.

7. An implantable medical device (IMD), comprising:

a housing enclosing memory, a processor and a protection circuit;

an electrode combination configured to at least one of i) sense physiologic signals or ii) deliver a therapy:

memory within the housing to store program instructions in connection with at least one of monitoring physiologic signals or delivering therapy; and a processor configured to execute the program instructions in connection with detecting physiologic signals along one or more sensing vectors defined by the electrode combination; and the protection circuit, comprising:

a bus controller including an address register, and unlock register and a protected register (PR) enable unit, the PR enable unit to set a protect enable signal to an access state based on content loaded into the unlock register; and a peripheral block including a protected register to retain content for operating the IMD, the peripheral block including a register access input to receive the protected enable signal; and a PR write control unit to enable an attempted write of the content from a data interface to the protected register when the protected enable signal has an access state, wherein the peripheral block further comprises:

a parity register configured to be set to a coherent value based on content of the protected register; and a comparator to compare content of the parity register and the protected register in connection with validating the content of the protected register.

8. The implantable medical device of claim 7, wherein the bus controller directs content conveyed over the data interface to one or more registers designated by the address register, the one or more registers including the protected register.

9. The implantable medical device of claim 7, wherein the PR enable unit includes a comparator to compare the content loaded into the unlock register with content loaded in the address register, the PR enable unit setting the protect enable signal to the access state when the content of unlock and address registers match.

10. The implantable medical device of claim 7, wherein the PR enable unit sets the protect enable signal to a deny state when the content of the unlock and address registers differ.

11. The implantable medical device of claim 7, wherein the peripheral block and bus controller are formed on a common integrated circuit.

12. The implantable medical device of claim 7, wherein the bus controller to automatically clear the unlock register, once the unlock register content is analyzed, to avoid analyzing the content of the unlock register associated with a first PR write request during a later second PR write request.

13. The implantable medical device of claim 7, wherein the peripheral block further comprises a parity register control unit that sets a content of the parity register to an incoherent value when the protected register is reset to a default content, the incoherent value representing an opposite of a coherent value corresponding to the default content.

14. A method to manage modifications to protected registers within an implantable medical device (IMD), comprising:

retaining first content in a protected register (PR) for operating the IMD;

receiving a PR write request representing an attempted write of second content to the protected register;

analyzing content of an unlock register associated with the protected register;

setting a protect enable signal to an access state or a deny state based on the content loaded into the unlock register;

enabling the attempted write of the second content to the protected register when the protected enable signal has the access state, wherein:

before the analyzing operation, the method further comprising: i) saving an initial content of the unlock register on an interrupt stack, the initial content independent of the PR write request; and ii) writing unlock content to the unlock register over the initial content; and after enabling the attempted write of the second content, the method further comprises popping the initial content from the interrupt stack and reloading the initial content to the unlock register.

15. The method of claim 14, wherein the analyzing comprises comparing the content of the unlock register to an address in an address register, the address designating the protected register.

16. The method of claim 14, further comprising once the unlock register content is analyzed, automatically clearing the unlock register to avoid analyzing the content of the unlock register associated with a first PR write request during a later second PR write request.

17. A circuit to manage modifications to protected registers within an implantable medical device (IMD), comprising:

a bus controller including an address register, and unlock register and a protected register (PR) enable unit, the PR enable unit to set a protect enable signal to an access state based on content loaded into the unlock register; and a peripheral block including a protected register to retain content for operating the IMD, the peripheral block including a register access input to receive the protected enable signal; and a PR write control unit to enable an attempted write of the content from a data interface to the protected register when the protected enable signal has an access state, wherein the peripheral block further comprises a parity register control unit that sets a content of the parity register to an incoherent value when the protected register is reset to a default content, the incoherent value representing an opposite of a coherent value corresponding to the default content.

18. The circuit of claim 17, wherein the unlock register is configured to receive a code authorizing a modification to a protected register having an address stored in the address register.

19. The circuit of claim 17, wherein the bus controller directs content conveyed over the data interface to one or more registers designated by the address register, the one or more registers including the protected register.

20. The circuit of claim 17, wherein the PR enable unit includes a comparator to compare the content loaded into the unlock register with content loaded in the address register, the PR enable unit setting the protect enable signal to the access state when the content of unlock and address registers match.

21. The circuit of claim 20, wherein the PR enable unit sets the protect enable signal to a deny state when the content of the unlock and address registers differ.

22. The circuit of claim 17, wherein the bus controller to automatically clear the unlock register, once the unlock register content is analyzed, to avoid analyzing the content of the unlock register associated with a first PR write request during a later second PR write request.

* * * * *